United States Patent [19]

Sawicki et al.

[11] Patent Number: 4,689,422
[45] Date of Patent: Aug. 25, 1987

[54] NOVEL LIGAND CATALYST SYSTEMS FORMED BY REACTION OF CARBONYL COMPOUNDS WITH ORGANOSILICON COMPOUNDS

[75] Inventors: Robert A. Sawicki, Wappingers Falls; Harry Chafetz, Glenham, both of N.Y.

[73] Assignee: Texaco Inc., White Plains, N.Y.

[21] Appl. No.: 813,910

[22] Filed: Dec. 27, 1985

[51] Int. Cl.$^4$ ............................................. C07C 68/00
[52] U.S. Cl. ................................. 558/277; 502/158; 556/418; 556/419
[58] Field of Search ........................................ 558/277

[56] References Cited

U.S. PATENT DOCUMENTS

| | | | |
|---|---|---|---|
| 3,846,468 | 11/1974 | Perrotti et al. | 558/277 X |
| 3,980,690 | 9/1976 | Cipriani et al. | 558/277 |
| 3,994,960 | 11/1976 | Yamazaki et al. | 558/277 X |
| 4,218,391 | 8/1980 | Romano et al. | 558/277 |

*Primary Examiner*—Michael L. Shippen
*Attorney, Agent, or Firm*—Robert A. Kulason; James J. O'Loughlin; Carl G. Seutter

[57] ABSTRACT

A novel ligand system useful in preparation of dimethyl carbonate is prepared by complexing a metal salt such as cuprous chloride $Cu_2Cl_2$ with a ligand formed by reacting a carbonyl-containing compound such as ethyl formate with an organosilicon compound such as ethyl formate with an organosilicon compound containing alkoxy and amine functionality, such as 3-aminopropyltriethoxysilane or [3-(2-aminoethyl)aminopropyl]trimethoxysilane.

11 Claims, No Drawings

NOVEL LIGAND CATALYST SYSTEMS FORMED BY REACTION OF CARBONYL COMPOUNDS WITH ORGANOSILICON COMPOUNDS

FIELD OF THE INVENTION

This invention relates to novel ligand catalyst systems. More particularly it relates to complexed metals bonded to inorganic oxide supports.

BACKGROUND OF THE INVENTION

The art of immobilizing various materials on solid supports permits attainment of the advantages of both homogeneous catalysts and heterogeneous catalysts. Illustrative of prior art directed to this art are (i) R. B. Merrifield J. Am. Chem. Soc. 85 2149 (1963); (ii) D. D. Whitehurst, CHEMTECH 44 (1980), (iii) P. Tundo et al J. Am. Chem. Soc. 101, 6606 (1979); (iv) U.S. Pat. No. 3,980,583; etc.

It is an object of this invention to provide a novel ligand catalyst system. Other objects will be apparent to those skilled in the art.

STATEMENT OF THE INVENTION

In accordance with certain of its aspects, this invention is directed to a process which comprises reacting in liquid phase:

(i) organosilicon amine 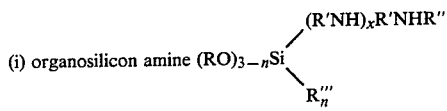

wherein R and R'' are hydrogen, alkyl, alkaryl, aralkyl, cycloalkyl, or aryl, R' is alkylene, alkarylene, aralkylene, cycloalkylene, or arylene, R''' is alkyl, alkaryl, aralkyl, aryl, or cycloalkyl, x is 0 or an integer, and n is an integer 0, 1, or 2, with (ii) a carbonyl-containing organic compound selected from the group consisting of carboxylic acids, carboxylic acid esters, ketones, aldehydes, and acid anhydrides thereby forming product

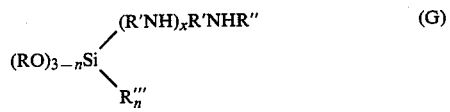 (G)

wherein G is a residue of said carbonyl-containing organic compound bonded to a nitrogen atom N, in place of a designated hydrogen atom, through a carbon atom.

In accordance, with certain of its other aspects, this invention is directed to a novel catalyst comprising, (i) an inert oxide substrate bearing on the surface thereof (ii) at least one residue

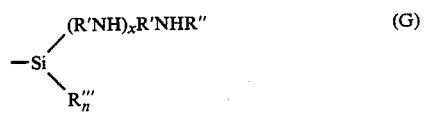 (G)

wherein
R'' is hydrogen, alkyl, alkaryl, aralkyl, cycloalkyl, or aryl;

R' is alkylene, alkarylene, aralkylene, cycloalkylene, or arylene;

R''' is alkyl, alkaryl, aralkyl, cycloalkyl or aryl; x is 0 or an integer; n is an integer 0, 1, or 2, G is a residue of a carbonyl-containing organic compound bonded to a nitrogen atom, in place of a hydrogen atom, through a carbon atom; and bonded thereto a metal salt.

DESCRIPTION OF THE INVENTION

The Organosilicon Compound

The organosilicon compound which may be used to form the ligands of this invention may be characterized by the formula

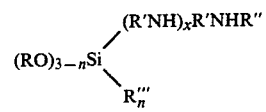

wherein R and R'' are selected from the group consisting of hydrogen, alkyl, alkaryl, aralkyl, cycloalkyl, and aryl, R''' is alkyl, aryl, or cycloalkyl, R' is a hydrocarbon selected from the group consisting of alkylene, alkarylene, aralkylene, cycloalkylene, an arylene; x is 0 or an integer and n is an integer 0, 1, or 2.

When R or R'' or R''' is alkyl, it may typically be methyl, ethyl, n-propyl, iso-propyl, n-butyl, i-butyl, sec-butyl, amyl, octyl, decyl, octadecyl, etc. When R or R'' or R''' is aralkyl, it may typically be benzyl, beta-phenylethyl etc. When R or R'' or R''' is cycloalkyl, it may typically be cyclohexyl, cycloheptyl, cyclooctyl, 2-metylcycloheptyl, 3-butylcyclohexyl, 3-methylcyclohexyl, etc. When R or R'' or R''' is aryl, it may typically by phenyl, naphthyl, etc. When R or R'' or R''' is alkaryl, it may be inertly substituted i.e. it may bear a non-reactive substitute such as alkyl, aryl, cycloalkyl, etc. The preferred groups may be lower alkyl, i.e. $C_1-C_{10}$ alkyl, groups (or groups derived therefrom) including e.g. methyl, ethyl, n-propyl, i-propyl, butyls, amyls, hexyls, octoyls, decyls, etc. R may preferably be ethyl; R' may preferably be propylene-$(CH_2)_3$.

When x is 0, the organosilicon may have the formula:

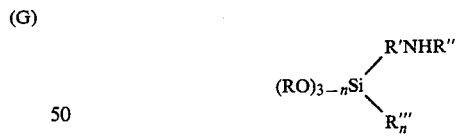

Illustrative organosilicon compounds which may be employed may be the following:

TABLE 3-aminopropyltriethoxysilane
3-aminopropyltrimethoxysilane

When x is an integer greater than 0, the organosilicon may typically have the formula:

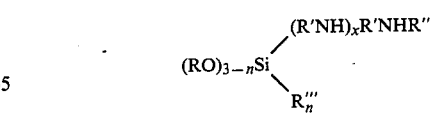

in which x is 1, etc.

Illustrative of these organosilicon compounds may be:

TABLE (aminoethylaminomethyl)phenethyltrimethoxysilane
[3-(2-aminoethyl)aminopropyl]methyldimethoxysilane
[3-(2-aminoethyl)aminopropyl]trimethoxysilane A preferred compound may be 3-aminopropyltriethoxysilane in which R is ethyl, R' is propylene $(CH_2)_3$, R" is hydrogen x is zero and n is zero. These compounds may be available commercially or they may be readily prepared.

The Carbonyl Compound

The carbonyl-containing organic compounds, which may be reacted with the organometallic compounds in practice of the process of this invention, may be typified by those containing the following functionality: carboxylic acid, carboxylic acid ester, ketone, aldehyde, acid anhydride, etc.

Illustrative carbonyl-containing organic compounds which may be employed may be the following:

TABLE acetic acid
benzoic acid

TABLE ethyl formate
ethyl acetoacetate

TABLE 2,4-pentanedione
2,6-hexanedione

TABLE salicylaldehyde
acetaldehyde

TABLE succinic anhydride
phthallic anhydride

THE SUBSTRATE

The substrate which may be employed in practice of the process of this invention include inorganic oxide substrates or supports, which are characterized by the presence of pendant surface hydroxyl groups.

The charge solid inorganic oxides which may be used as substrates in practice of the process of this invention may include a wide variety or porous refractory oxides typified by those which may commonly be used as inert catalyst supports. Although they may be used in in pure form or as mixtures, more consistent results may be attained by the use of one species of pure porous refractory metal oxide. Illustrative of the porous refractory solid inorganic metal (including metalloid) oxides may be oxides of boron, magnesium, aluminium, silicon, phosphorus, calcium, titanium, vanadium, chromium, maganese, iron, cobalt, nickel, copper, zinc, arsenic, cadmium, barium, etc. It will be apparent that certain oxides typified by those of sodium may be too active under reaction conditions and may not be employed. Others may be too expensive. The preferred solid refractory oxides are those commonly referred to as inert and which have heretofore been proposed for use as catalyst supports. Most preferred are aluminum oxide ($Al_2O_3$) and silicon dioxide ($SiO_2$). Complex oxides may be employed viz: silica-magnesia; etc. Silicon dioxide is a preferred charge solid inorganic porous refractory metal oxide. A preferred form of silica is that referred to as silica gel.

It is also possible to use as substrates refractory oxides which are crystalline aluminosilicates including synthetic zeolites typified by zeolites X, Y, ZSM-4, ZSM-5, ZSM-11, ZSM-21, etc. as well as naturally occurring zeolites such as erionite, faujasite, mordenite, etc.

The surface of the charge porous refractory inorganic metal oxide bears a plurality of pendant hydroxyl groups. Although it may be possible to use the porous refractory oxides as they are obtained, it is preferred to pretreat them preferably by heating to drive off adsorbed water, at 50° C.–450° C., say 200° C. for 1–24 hours, say 6 hours at atmospheric pressure. In the case of silica, it may alternatively be desirable to pretreat by reaction in aqueous medium in liquid phase with a Bronsted acid, typically at 25° C.–100° C., say 100° C. for 1–24 hours, say 4 hours. Illustrative Bronsted acids include hydrogen halides, preferably hydrogen chloride.

During this pretreatment, it appears that additional hydroxyl groups may be made available for reaction. Pretreatment is not necessary however.

THE METAL SALT

Typical metal salts which may be used may be salts of metals of Group IB (Ag or Au or preferably Cu) or of Group VIII (Fe, Co, Ni, Ru, Rh, Pd, Os, Ir, Pt).

The metal salts may already have ligands attached to them—ionic, neutral, or mixed—typified by ammonia, phosphine, carbon monoxide, olefins, etc. The anion may preferably be halide (fluoride, chloride, bromide, or iodide), halogen-like (cyanide, cyanate, thiocyanate) etc, or others typified by nitrate, sulfate, phosphate, sulfide, carbonate, or carboxylate, (either acidic, basic, or neutral).

Illustrative salts may include (the first four being preferred):

TABLE $Cu_2Cl_2$
$CuCl_2$
$CuCl (OCH_3)$
$FeCl_2$
$PdCl_2$
$NiCl_2$
$CuBr_2$
$CuSO_4$
$RhCl_3$
$RuI_3$

In practice of the process of this invention, it is possible to form the desired product by various routes including any of the following routes:

(i) reacting the organosilicon amine A with the carbonyl-compound B to form the ligand, then reacting this with the support C to form the immobilized ligand, and then reacting with the metal salt D to form the immobilized metal complex—viz ABCD;

(ii) reacting the organosilicon amine A with the carbonyl-compound B and the metal salt D to form a preformed complex and then reacting with the support C to form the immobilized metal complex—viz ABDC;

(iii) adding all the ingredients to the reaction vessel simultaneously;

(iv) reacting the organosilicon amine A with the support C, then reacting with the carbonyl compound B, followed by reacting with the metal salt D—viz ACBD.

Other equivalent variants will be apparent to those skilled in the art.

Although the order of addition of the several components may be modified, it is preferred that the ligand be formed first by reaction of organosilicon compound A and carbonyl-containing organic compound B, then this be reacted with metal salt D and then the solid oxide C be added, i.e. the ABDC sequence.

REACTION OF ORGANOSILICON AND CARBONYL COMPOUND

The reaction between the organosilicon compound and the carbonyl-containing organic compounds in practice of the process of this invention may be carried out by use of 0.1–10 moles, say 1 mole of carbonyl-containing compound per mole of organosilicon compound.

The reaction may be carried out in the presence of solvent if desired, typically lower alcohols such as ethanol or hydrocarbons such as hexane. Preferably reaction is carried out in liquid phase at 0° C.–150° C., say 0° C. and atmospheric pressure by adding one reactant, typically the organosilicon compound, slowly with agitation over 5–120 minutes to the carbonyl-containing organic compound.

After addition is complete, the reaction mixture is heated to reflux, typically 50° C.–150° C., say 70° C. for 1–24 hours, say 3 hours. At the conclusion of the reaction, the solvent may be recovered by distillation and the excess of carbonyl-containing compound may also be similarly removed.

LIGAND PRODUCTS

The ligands so prepared may typically be recovered as high boiling liquids. Typical of the reactions may be the following:

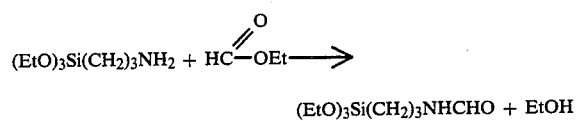

Illustrative products which may be prepared include the following:

(EtO)$_3$Si(CH$_2$)$_3$NHCHO    A.

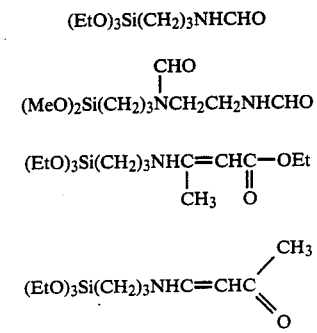

(EtO)$_3$Si(CH$_2$)$_3$NHCCH$_2$CH$_2$COOH (with C=O)    E.

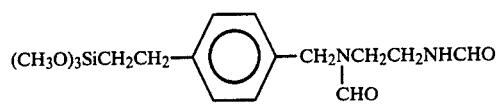

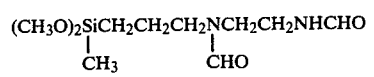

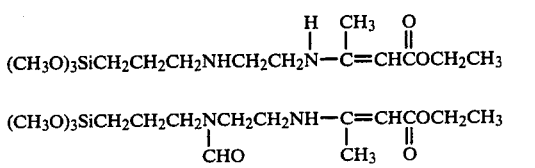

In practice of the preferred mode of carrying out the process of this invention, the ligand which has been formed from the organometallic silicon compound and the carbonyl-containing organic compound is reacted with a metal salt.

REACTION BETWEEN SALT AND LIGAND

Reaction, in the preferred embodiment, between the metal salt and the ligand is preferably effected by addition of one mole of the former (dissolved in solvent such as absolute ethanol) to 0.01–10 moles, say 1 mole of the latter (also dissolved in solvent such as absolute ethanol). Reaction is effected at −50° C. to 50° C., say 20° C. and preferably atmospheric pressure pressure over 5–180 minutes, say 60 minutes.

At the end of this reaction period, there is added hydrocarbon solvent (preferably toluene) in amount of 50–10,000 ml, say 500 ml per mole of ligand and there is also added inorganic oxide in amount of 1–5000 g, say 700 g per mole of ligand.

The mixture is heated to reflux at 50° C.–150° C., say 100° C. for 5–600 minutes, say 240 minutes during which distillate is removed and replaced with an equivalent amount of e.g. toluene. The procedure is repeated twice during which total time of reflux of 4 hours, the toluene-alcohol azeotrope is removed to drive the reaction to completion.

The mixture is cooled to ambient temperature of 20° C.–30° C., say 25° C. and filtered—the solid being washed with fresh toluene and then with ethanol. Product after drying at room temperature under vacuum is typically a colored power obtained in yield of 80–100%, say 90% based on charged reactants.

The product of this invention according to certain of its aspects may be a complex of a metal salt with an inorganic oxide bearing immobilized thereon a ligand of a carbonyl-containing organic compound and a primary or secondary amine of an organosilicon-bond-forming atom.

Typical of these products may be the following:

TABLE

| Carbonyl-Ctg Compound | Amine | Metal Salt | Inorganic Oxide |
|---|---|---|---|
| Ethyl Formate | 3-aminopropyltriethoxysilane | $CuCl_2$ | $SiO_2$ |
| Ethyl Formate | [3-(2-aminoethyl)aminopropyl]trimethoxysilane | $FeCl_2$ | $SiO_2$ |
| Ethyl Acetoacetate | 3-aminopropyltriethoxysilane | $PdCl_2$ | $SiO_2$ |
| 2,4-pentanedione | 3-aminopropyltriethoxysilane | $NiCl_2$ | $SiO_2$ |
| salicylaldehyde | 3-aminopropyltriethoxysilane | $CuCl_2$ | $Al_2O_3$ |
| succinic anhydride | 3-aminopropyltriethoxysilane | $CuCl_2$ | $SiO_2$ |
| Ethyl Formate | [3-(2-aminoethyl)aminopropyl]trimethoxysilane | $CuCl\ (OCH_3)$ | $SiO_2$ |

OXIDATIVE CARBONYLATION

It is a feature of the process of this invention that these novel products may be used as catalysts for various reactions depending upon the specific composition. They may be found to be useful in oxidative carbonylation reactions typified by the preparation of dimethyl carbonate from methanol. A preferred embodiment may be that last set forth in the above table.

In a typical oxidative carbonylation, the charge, e.g. methanol may be added to a reaction vessel with the catalyst and, after flushing with carbon monoxide, pressured to 100–5000 psig, preferably 300–1500 psig, say 1000 psig with carbon monoxide at 0° C.–50° C., say 25° C.

The reaction mixture may be maintained at 50° C.–150° C., say 100° C. for 1–24 hours, say 8 hours with agitation. After cooling to ambient temperature, the reaction mixture, analyzed by gas chromatography (using isooctane as an internal standard), is found to contain dimethyl carbonate in yield (based on methanol) of 18%–36%, say 36% using $CuCl_2$.

In the absence of ligands or supports, $CuCl_2$ gives yields of dimethyl carbonate of ca 12% or less.

It is a feature of the process of this invention that yield of product in the oxidative carbonylation reaction may be substantially increased if the metal salt, employed in a lower valence state, is oxidized to a higher valence state in the presence of the charge which is to be oxidatively carbonylated.

In one preferred embodiment, the catalyst may be formed from cuprous chloride (e.g., an immobilized cuprous chloride complex of silicon dioxide bearing immobilized thereon a ligand of ethyl formate and [3-(2-aminoethyl)aminopropyl]trimethoxysilane).

This lower valent catalyst may be added to the reaction vessel together with solvent (preferably methanol). The cuprous ion may be oxidized as by passing dry air through the reaction mixture at 0° C.–50° C., say 45° C. for 1–24 hours, say 8 hours. After reaction with carbon monoxide and methanol as described above, analysis by gas chromatography (using isooctane as an internal standard) showed attainment of a yield of dimethyl carbonate based on copper salt charged, of 33%–83%, say 83%.

It is a particular feature of the process of this invention that it may be carried out in a continuous manner. In this continuous process, the catalyst may for example be a complex (prepared from cuprous chloride $Cu_2Cl_2$, with silicon dioxide on which is immobilized a ligand of ethyl formate and [3-(2-aminoethyl)aminopropyl]trimethoxysilane in the form of a packed bed of particles of about 5–6 mm diameter.

Air may be passed upwardly through the bed. Reaction is carried out at 50° C.–125° C., say 90° C. and 300–1500 psig, say 600 psig.

As these compounds pass through the catalyst bed, the carbon monoxide and the methanol react in liquid phase to form dimethyl carbonate in the presence of oxygen:

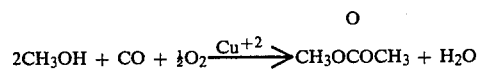

It also appears that the metal salt (e.g. copper (I) chloride) may participate in the reaction as follows (L* represents the supported ligand):

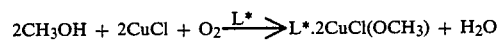

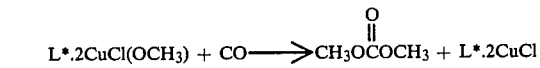

Product withdrawn from the reactor includes dimethyl carbonate and water. Anhydrous dimethyl carbonate may be obtained by distillation.

Dimethyl carbonate may be employed as an additive to hydrocarbon fuels including gasolines; and it also finds use as an intermediate in many chemical reactions wherein it may replace phosgene.

DESCRIPTION OF SPECIFIC EMBODIMENTS

Practice of the process of this invention will be apparent to those skilled in the art from the following examples.

All reactions were carried out using reagent grade materials with no prior purification. The catalysts were routinely prepared under an inert atmosphere.

CATALYST PREPARATION—LIGAND FORMATION

Example I

Amide Ligand. Reaction of 3-Aminopropyltriethoxysilane with ethyl formate

A reaction flask containing 220 ml (2.73 mol) ethyl formate was cooled to 0° C. in an ice bath; and 3-aminopropyltriethoxysilane (120 g, 0.54 mol) was added slowly with stirring. After complete addition, the mixture was heated at reflux for ten hours. The excess ethyl formate was stripped from the product on a rotary evaporator at room temperature under vacuum to afford 147 g of an orange liquid. Infrared (IR) and nuclear magnetic resonance (NMR) spectroscopy were consistent with the proposed amide ligand structure.

Example II

Diamide Ligand. Reaction of [3-(2-aminoethyl)-aminopropyl]triethoxysilane with ethyl formate To a flask containing 150 ml (1.86 mol) ethyl formate cooled as in Example I was added 30 g (0.14) 3-[2-aminoethyl)-aminopropyl]trimethoxysilane. After ten hours at reflux, the excess ethyl formate was removed by stripping as in Example I to yield 39 g of a yellow liquid. Both IR and NMR analyses were consistent with the proposed structure.

Example III

Enaminone Ligand. Reaction of 3-Aminopropyltriethoxysilane with ethyl acetoacetate Into a flask containing a stirrer, addition funnel and Dean Stark trap with reflux condenser was added 15 g (0.12 mol) ethyl acetoacetate, 25 ml absolute ethanol, and 150 ml heptane. While stirring, 25 g (0.11 mol) 3-aminopropyltriethoxysilane was added slowly at room temperature. After complete addition, the mixture was heated at reflux for 3 hours with continuous removal of the bottom layer that was collected in the Dean-Stark trap (19 ml, calc. 2.8 ml water, 0.16 mol). The resulting mixture was stripped of residual solvent at 50° C. under vacuum to afford 37 g of a pale yellow liquid. Both IR and NMR analyses were consistent with the proposal structure.

Example IV

Enaminone Ligand. Reaction of 3-aminopropyltriethoxysilane with 2,4-pentanedione Into a flask fitted as in Example III was added 11 g (0.11 mol) 2,4-pentanedione, 25 ml absolute ethanol, and 150 ml heptane. While stirring, 25 g (0.11 mol) 3-aminopropyltriethoxysilane was added slowly at room temperature. The mixture was heated to reflux for 3 hours removing 13 ml of the bottom azeotropic layer (calc. 2 ml water, 0.11 mol). Stripping at 50° C. under vacuum yielded 31 g of a brown liquid. Both IR and NMR analyses were consistent with the proposed structure.

Example V

Amide-Acid Ligand. Reaction of 3-aminopropyltriethoxysilane with succinic anhydride Into a flask fitted as in Example III was added 11 g (0.11 mol) succinic anhydride, 25 mol absolute ethanol, and 150 ml heptane. While stirring, 25 g (0.11 mol) 3-aminopropyltriethoxysilane was added slowly at room temperature. The mixture was heated at reflux for 3 hours with no formation of a lower azeotropic layer. Stripping at 50° C. under vacuum afforded 39 g of a viscous yellow liquid. Both IR and NMR analyses were consistent with the proposed structure.

Example VI

Diamide Ligand. Reaction of (aminoethylaminomethyl)phenethyltrimethoxysilane with ethyl formate To a flask containing 15 g (0.045 mol) (aminoethylaminoethyl)phenethyltrimethoxysilane cooled as in Example I was added 100 ml (1.24 mol) ethyl formate. After ten hours at reflux, the excess ethyl formate was stripped to yield 20 g of a viscous yellow liquid. Both IR and NMR analyses were consistent with the proposed structure.

Example VII

Diamide Ligand. Reaction of [3-(2-aminoethyl)aminopropyl]methyldimethoxysilane with ethyl formate To a flask containing 10 g (0.048 mol) (3-(2-aminoethyl)aminopropyl)methyldimethoxysilane cooled as in Example I was added 100 ml (1.24 mol) ethyl formate. After ten hours at reflux, the excess ethyl formate was stripped to yield 14 g of a light orange liquid. Both IR and NMR analyses where consistent with the proposed structure.

Example VIII

Triamide Ligand. Reaction of trimethoxysilylpropyldiethylenetriamine with ethyl formate To a flask containing 375 ml (4.65 mol) ethyl formate cooled as in Example I was added 50 g (0.19 mol) trimethoxysilylpropyldiethylenetriamine. After ten hours at reflux, the product was stripped to yield 58 g of an orange/brown viscous liquid. Both IR and NMR analyses were consistent with a triamide product.

Example IX

Enaminone Ligand. Reaction of [3-(2-aminoethyl)aminopropyl]trimethoxysilane with ethyl acetoacetate To a flask containing 17.5 g (0.135 mol) ethyl acetoacetate, 150 ml hexane, and 25 ml ethanol cooled as in Example I was added 30 g (0.14 mol) [3-(2-aminoethyl)aminopropyl]-trimethoxysilane. The reaction vessel was heated at reflux for 3 hours and the contents, after cooling, were filtered through alumina. Stripping residual solvent at 50° C. afforded 44 g of a light orange liquid. Both IR and NMR analyses were consistent with an enaminone product.

Example X

Enaminone/Amide Ligand. Reaction of [3-(2-aminoethyl)aminopropyl]trimethoxysilane with ethyl acetoacetate and ethyl formate To a flask containing 8.75 g (0.067 mol) ethyl acetoacetate, 175 ml hexane, and 25 ml ethanol cooled as in Example I was added 30 g (0.14 mol) [3-(2-aminoethyl)aminopropyl]trimethoxysilane. After 3 hours at reflux the contents were filtered and the filtrate stripped at 50° C. affording a light yellow liquid product. To this material was added 150 ml (1.86 mol) ethyl formate slowly. The reaction mixture was heated at reflux for 10 hours, cooled, filtered, and the excess ethyl formate stripped off at 50° C. The product (37 g) was a light yellow liquid whose IR and NMR spectra were consistent with an enaminone/amide structure.

LIGAND ATTACHMENT

Example XI

Reaction of product of Example II with silica gel

To a 1 liter 3-neck flask fitted with a mechanical stirrer and Dean-Stark trap with reflux condenser was added 100 g silica gel, 400 ml toluene and 34 g (0.14 mol) of the product of Example II. The mixture was heated at reflux for two hours and 50 ml distillate was collected and discarded. After an additional two hours at reflux and an additional 50 ml distillate removed, the pot was cooled to room temperature. After filtering, the resulting white powder was Soxhlet extracted with methanol for 24 hours. Subsequent drying at 50° C. under vacuum afforded 117 g of a white powder containing 8.54 percent carbon adn 2.37 percent nitrogen.

Example XII

Reaction of product of Example VIII with silica gel

To a flask fitted as in Example XI was added 50 g silica gel, 250 ml toluene and 21 g (0.06) Example VIII. The procedure and work-up followed as in Example XI. Drying at 50° C. under vacuum afforded 64 g of a pale yellow powder containing 14.37 percent carbon and 4.24 percent nitrogen.

Example XIII

Reaction of product of Example II with titanium dioxide

To a flask fitted as in Example XI was added 100 g titanium dioxide, 400 ml toluene and 34 g (0.12 mol) of the product of Example II. The procedure and work-up followed as in Example XI. Drying at 50° C. under vacuum afforded 110 g of a white powder containing 4.99 percent carbon and 1.35 percent nitrogen.

Example XIV

Reaction of product of Example II with aluminum oxide

To a flask fitted as in Example XI was added 100 g aluminum oxide, 400 ml toluene, and 34 g (0.12 mol) of the product of Example II. The procedure and work-up followed as in Example XI. Drying at 50° C. under vacuum afforded 110 g of a white powder containing 5.12 percent carbon and 1.31 percent nitrogen.

Example XV

Reaction of product of Example II with magnesium silicate

To a flask fitted as in Example XI was added 100 g magnesium silicate, 400 ml toluene and 34 g (0.12 mol) of the product of Example II. The procedure and work-up followed as in Example XI. Drying at 50° C. under vacuum afforded 113 g of a white powder containing 5.48 percent carbon and 1.41 percent nitrogen.

Example XVI

Reaction of product of Example II with alumina extrudates

To a flask fitted as in Example XI was added 50 g alumina (⅛"×1/16" extrudate, 255 m²/g), 200 ml toluene, and 17 g (0.06 mol) of the product of Example II. The procedure and work-up were similar to Example XI except there was no stirring during reaction. Drying at 50° C. under vacuum afforded 67 g of a white extrudate containing 5.89 percent carbon and 1.61 percent nitrogen.

Example XVII

Reaction of Example VI with silica gel

To a flask fitted as in Example XI was added 75 g silica gel, 300 ml toluene, 25 ml methanol and 19 g of the product of Example VI. After removing an initial 25 ml distillate the procedure and work-up followed as in Example XI. Drying at room temperature under vacuum afforded 87 g of a white powder containing 8.15 percent carbon and 1.20 percent nitrogen.

Example XVIII

Reaction of Example VII with silica gel

To a flask fitted as in Example XI was added 50 g silica gel, 300 ml toluene, 25 methanol and 13 g of the product of Example VII. The procedure and work-up followed as in Example XI. Drying at room temperature under vacuum afforded 55 g of a white powder containing 7.26 percent carbon adn 1.97 percent nitrogen.

Example XIX

Reaction of Example IX with silica gel

To a flask fitted as in Example XI was added 50 g silica gel, 250 ml toluene and 17 g (0.05 mol) of the product of Example IX. The procedure and workup followed as in Example XI. Drying at 50° C. under vacuum afforded 50 g of a light yellow powder containing 6.77 percent carbon and 1.55 percent nitrogen.

Example XX

Reaction of Example X with silica gel

To a flask fitted as in Example XI was added 50 g silica gel, 250 ml toluene and 12 g of the product of Example X. The procedure and workup followed as in Example XI. Drying at 50° C. under vacuum afforded 60 g of a light yellow powder containing 7.23 percent carbon and 1.69 percent nitrogen.

CATALYST PREPARATION—METAL COMPLEXATION

Example XXI

Copper Salt. Reaction of Cupric Chloride with product of Example I and attachment of Silica Gel Into a flask fitted with an addition funnel, Dean-Stark trap and stirrer was added 6.8 g (0.027 mol) of the product of Example I and 25 ml absolute ethanol. Cupric chloride (2.1 g, 0.016 mol) was dissolved in 25 ml absolute ethanol and this solution added slowly to the pot at room temperature. After addition, the mixture was stirred one hour at room temperature. Toluene (150 ml) was added along with 20 g silica gel. The solution was heated at reflux for one hour and 25 ml distillate was removed. Fresh toluene (25 ml) was added to the pot and the procedure repeated 3 more times (Total—4 hours reflux, 100 ml distillate removed, 100 ml fresh toluene added). After cooling, the mixture was filtered and the solid washed slowly with fresh toluene (50 ml) and then with ethanol (50 ml). The solid was then dried at room temperature under vacuum to yield a yellow powder, 26 g, which contained 7.71 percent carbon, 1.38 percent nitrogen and 2.27 percent copper.

Example XXII

Iron Salt. Reaction of Ferrous Chloride with product of Example I and attachment to Silica Gel The procedure of Example XXI was followed with 2.0 g (0.06 mol) ferrous chloride ($FeCl_2$). Drying at room temperature under vacuum afforded a light orange powder (28.8 g) containing 5.10 percent carbon, 1.26 percent nitrogen, and 2.4 percent iron.

Example XXIII

Palladium Salt. Reaction of Palladium Chloride with product of Example I and attachment to Silica Gel The procedure of Example XXI was followed with 2.8 g (0.016 mol) palladium chloride (PdCl$_2$). Drying at room temperature under vacuum afforded a dark brown powder (27.6 g) containing 4.96 percent carbon, 1.32 percent nitrogen, and 2.3 percent palladium.

Example XXV

Nickel Salt. Reaction of Nickel Chloride with product of Example I and attachment to Silica gel The procedure of Example XXI was followed with 3.7 g (0.016 mol) nickel chloride hexahydrate (NiCl$_2$.6-H$_2$O). Drying at room temperature under vacuum afforded a light green powder (31.1 g) containing 5.09 percent carbon, 1.24 percent nitrogen, and 2.5 percent nickel.

Example XXVI

Copper Salt. Reaction of Cupric Chloride with product of Example II and attachment to silica gel The procedure of Example XXI was followed using 34 g (0.12 mol) catalyst from Example II, 75 ml ethanol, 100 g silica gel and 21 g (0.16 mol) cupric chloride. Drying at room temperature under vacuum afforded 152 g of a gold powder containing 7.91 percent carbon, 1.93 percent nitrogen, and 5.2 percent copper.

Example XXVI

Copper Salt. Reaction of Cupric Chloride with product of Example III and attachment to silica gel Into a flask fitted as in Example XXI was added 9 g (0.027 mol) of the product of Example III and 25 ml absolute ethanol. A mixture of cupric chloride (3.6 g, 0.027 mol) in 25 ml absolute ethanol was added slowly over 30 minutes. After stirring at room temperature for one hour, toluene (150 ml) and silica gel (20 g) were added and the procedure followed as in Example XXI. Drying at room temperature under vacuum afforded 26 g of a dark green powder containing 6.27 percent carbon, 1.0 percent nitrogen and 5.0 percent copper.

Example XXVII

Copper Salt. Reaction of Cupric Chloride with product of Example IV and attachment to Silica Gel Into a flask fitted as in Example XXI was added 8.2 g (0.027 mol) Example IV and 25 ml absolute ethanol. Cupric chloride (3.6 g, 0.027 mol) in ethanol (25 ml) was added slowly and the procedure of Example XXI was followed using toluene and silica gel (20 g). Drying at room temperature under vacuum afforded 26 g of a dark gold powder containing 6.99 percent carbon 0.96 percent nitrogen, and 4.5 percent copper.

Example XXVIII

Copper Salt. Reaction of Cupric Chloride with product of Example V and attachment to silica gel Into a flask fitted as in Example XXI containing 8.6 g (0.027 mol) Example V and 25 ml ethanol was added 3.6 g (0.027 mol) cupric chloride in 25 ml ethanol. The procedure of Example XXI was followed using toluene and silica gel (20 g). Drying at room temperature under vacuum afforded 25 g of a gold powder containing 8.58 percent carbon, 1.13 percent nitrogen, and 2.1 percent copper.

Example XXIX

Copper Salt. Reaction of Cupric Chloride with product of Example IV and attachment to titanium dioxide The procedure of Example XXVII was followed using 20 g titanium dioxide instead of silica gel. The dried light brown powder (22 g) contained 2.81 percent carbon, 0.60 percent nitrogen and 4.2 percent copper.

Example XXX

Copper Salt. Reaction of Cupric Chloride with product of Example IV and attachment to alumina The procedure of example XXVII was followed using 20 g alumina instead of silica gel. The dried dark brown powder (26.5 g) contained 4.42 percent carbon, 0.86 percent nitrogen, and 5.9 percent copper.

Example XXXI

Amine Ligand. Reaction of 3-Aminopropyltriethoxysilane with silica gel

Into a flask fitted with a stirrer and Dean Stark trap with reflux condenser was added 400 g silica gel, 1700 ml toluene, and 120 g (0.54 mol) 3-aminopropyltriethoxysilane. After heating to reflux for one hour 100 ml distillate was removed, and the mixture heated an additional two hours at reflux. A second 100 ml of distillate was removed, the pot heated an additional one hour at reflux and following filtration, the solid was washed with toluene (250 ml) and diethyl ether (250 ml). The white filer cake was dried at 75° C. under vacuum to yield 459 g of a white powder containing 4.91 percent carbon and 1.62 percent nitrogen.

Example XXXII

Enaminone Ligand-Copper Salt. Reaction of 2,4-Pentanedione with product of Example XXXI followed by complexation of cupric chloride Into a flask fitted as in Example XXXI was added 300 ml heptane, 40 g of Example XXXI, and 6.4 g of acetylacetone (2,4-pentanedione). The solution was heated to reflux for three hours removing the botton layer of the azeotrope (1.2 ml). After filtering, the solid was washed with heptane (50 ml) and diethyl ether (100 ml) and dried under vacuum at room temperature laving 42 g of a pale yellow powder containing 10.85 percent carbon and 1.57 percent nitrogen. Twenty grams of this powder was then charged into a flask fitted with a stirrer and addition funnel and 75 ml ethanol added. Cupric chloride (4.4 g) was dissolved in 25 ml ethanol and this mixture added slowly to the pot at room temperature over 30 minutes. After stirring an additional 2 hours the solid was filtered, washed with fresh ethanol (50 ml) and dried at room temperature under vacuum affording 22 g of a brown powder containing 9.17 percent carbon, 1.43 percent nitrogen and 2.6 percent copper.

Example XXXIII

Schiff Base Ligand-Copper Salt. Reaction of Salicylaldehyde with the product of Example XXXI followed by complexation of cupric chloride Same procedure was followed as in Example XXXI using 7.8 g salicylaldehyde. Initial reaction yielded a bright yellow powder (44 g) containing 12.93 percent carbon and 1.47 percent nitrogen. Complexation with cupric chloride afforded a brown powder (22 g) containing 12.45 percent carbon, 1.43 percent nitrogen, and 3.3 percent copper.

Example XXXIV

Diamide Ligand-Copper Salt. Attachment of the product of Example II to silica gel followed by complexation of cupric chloride Into a flask fitted with a stirrer and Dean Stark trap with reflux condenser was added 100 g silica gel, 500 ml toluene, adn 30 g of Example II. The mixture was heated at reflux a total of four hours removing 25 ml of distillate at the end of one and three hours. After filtering, the white solid was washed with toluene (100 ml) and diethyl ether (100 ml). Drying under vacuum at 75° C. afforded 119 g of a white powder containing 7.55 percent carbon and 2.07 percent nitrogen. Into a flask containing 100 g of the above solid and 225 ml ethanol was added a solution of 20 g cupric chloride in 75 ml ethanol. After stirring at room temperature for two hours the mixture was filtered, the solid washed with fresh ethanol (100 ml), and dried at room temperature under vacuum to yield 110 g of a fold colored powder containing 6.28 percent carbon, 1.89 percent nitrogen, and 8.2 percent copper.

Example XXXV

Copper Salt. Reaction of cuprous chloride with the product of Example XI followed by oxidation in the presence of methanol Into a flask fitted with a mechanical stirrer, air inlet (tube, thermometer, and reflux condenser was added 30 g. Example XI, 6 g (0.06 mol) cuprous chloride and 180 ml methanol. Dry air was run through the heterogeneous mixture at 535 ml/min and the pot heated at 45° C. for 6 hours. The product was filtered and the resulting filter cake Soxhlet extracted with methanol for six hours. Drying at room temperature under vacuum afforded 37 g of a light green powder containing 8.14 percent carbon, 2.21 percent nitrogen and 8.0 percent copper.

Example XXXVI

Into a 2 liter single neck flask was added 500 g of the product of Example XI, 100 g cuprous chloride and 1300 ml acetonitrile. After stirring two hours at room temperature the solvent was stripped using a rotary evaporator at 50° C. under vacuum. The resulting powder (623 g) contained 8.06 percent carbon, 2.13 percent nitrogen and 6.87 percent copper.

To a flask containing 1500 ml methanol and equipped with a stirrer, reflux condenser, thermometer and air inlet was added 500 g of the above powder. The pot was heated at 45° C. for 6 hours with an air flow of 550 ml/min. After filtering, the green powder was Soxhlet extracted with methanol for 6 hours. Drying at room temperature under vacuum afforded 489 g of a light green powder containing 7.89 percent carbon, 2.19 percent nitrogen and 6.10 percent copper.

CATALYST EVALUATION—DIMETHYL CARBONATE PRODUCTION

Example XXXVII

Oxidative Carbonylation of Methanol using the copper catalyst from Example XXI

Into a 1 liter Hastelloy autoclave fitted with a glass liner was added 125 ml methanol and 25 g of the product of Example XXI. The reactor was flushed with carbon monoxide and pressurized to 1000 psig carbon monoxide at room temperature. The mixture was subsequently heated at 100° C. for eight (8) hours. After cooling the liquid was analyzed by gas chromatography using isoctane as an internal standard and shown to contain a 25% yield of dimethyl carbonate based on the copper salt charged.

Example XXXVIII

Oxidative carbonylation of methanol using the copper complex from Example XXXV

Into a 1 Hastelloy autoclave fitted with a glass liner was added 150 ml methanol and 30 g of the product of Example XXXV. The reactor was flushed with CO and pressurized to 1000 psig. After heating at 100° C. for eight hours the mixture was found to contain 83% yield of dimethyl carbonate based on gas chromatographic analyses and charged copper salt.

Example XXXIX

Oxidative carbonylation of methanol using the copper complex from Example XXXVI

Into a 1 liter Hastelloy autoclave with a glass liner was added 125 ml methanol and 30 g of the product of Example XXXVI. After flushing with carbon monoxide, the reactor was pressurized to 600 psig CO and heated at 100° C. for one hour. After venting, the liquid product was analyzed by gas chromatography and found to contain a 76% yield of dimethyl carbonate based on charged copper salt using isoctane as the internal standard.

DIETHYL CARBONATE PRODUCTION

Into a 1 liter Hastelloy autoclave with glass liner was added 125 ml ethanol and 30 g of the product of Example XXXVI. After flushing with carbon monoxide, the reactor was pressurized to 1000 psig CO and heated at 100° C. for eight hours. The liquid product contained a 45% yield of diethyl carbonate based on charged copper salt using gas chromatographic analysis and isoctane as the internal standard.

Although this invention has been illustrated by reference to specific embodiments, it will be apparent to those skilled in the art that various changes and modifications may be made which clearly fall within the scope of this invention.

We claim:

1. The process which comprises oxycarbonylating a lower alkanol with carbon monoxide and oxygen at 50° C.–150° C. and 300–1500 psig for 1–24 hours in the presence of a functionalized inorganic oxide substrate composition comprising (i) an inert oxide substate bearing on the surface thereof
   (ii) at least one residue $$-Si\diagup^{(R'NH)_xR'NR''}_{\diagdown R'''_n} \qquad (G)$$

wherein
   R'' is hydrogen, alkyl, alkaryl, aralkyl, cycloalkyl, or aryl;

R' is alkylene, alkarylene, aralkylene, cycloalkylene, or arylene;

R''' is alkyl, alkaryl, aralkyl, cycloalkyl, or aryl;

x is 0 or an integer;

n is an integer 0, 1, or 2;

G is a residue of a carbonyl-containing organic compound selected from the group consisting of carboxylic acids, carboxylic acid esters, ketones, aldehydes, and acid anhydrides, said residue being bonded, through a carbon atom, to a nitrogen atom; and bonded thereto a metal salt.

2. The process claimed in claim 1 wherein said inorganic oxide substrate comprises a porous refractory solid inorganic oxide of boron, magnesium, aluminum, silicon, phosphorus, calcium, titanium, vanadium, chromium, manganese, iron, cobalt, nickel, copper, zinc, arsenic, cadmium, or barium.

3. The process claimed in claim 2 wherein said metal salt is a halide of a metal of Groups I B or VIII of the Periodic Table.

4. The process claimed in claim 2 wherein said metal salt is cupric chloride $CuCl_2$.

5. The process claimed in claim 2 wherein said metal salt is cuprous chloride $Cu_2Cl_2$.

6. The process claimed in claim 2 wherein said residue G is a residue of ethyl formate, ethyl acetoacetate, 2,4-pentanedione, or succinic anhydride.

7. The process claimed in claim 1 wherein said inorganic oxide substrate comprises at least one of silica or alumina.

8. The process claimed in claim 1 wherein said inorganic oxide substrate comprises a crystalline aluminosilicate.

9. The process which comprises oxycarbonylating a lower alkanol with carbon monoxide and oxygen at 50° C.–150° C. and 300–1500 psig for 1–24 hours in the presence of a functionalized inorganic oxide substrate composition comprising silica gel bearing on the surface thereof a ligand of (i) 3-aminopropyltriethoxy silane and (ii) ethyl formate, succinic anhydride, 2,4-pentanedione, or ethyl acetoacetate; and bonded thereto a metal salt.

10. The process as claimed in claim 9 wherein said metal salt is a salt of copper.

11. The process as claimed in claim 9 wherein said metal salt is a chloride of copper, iron, nickel, or palladium.

* * * * *